United States Patent
Meyler et al.

(10) Patent No.: US 6,764,215 B2
(45) Date of Patent: Jul. 20, 2004

(54) METHOD, A MEASURING CELL AND A SYSTEM FOR MEASURING VERY SMALL HEAT CHANGES IN A SAMPLE

(75) Inventors: Phil Meyler, Cardiff (GB); Rudi Labarbe, Cardiff (GB)

(73) Assignee: Amersham Biosciences UK Ltd., Amersham (GB)

( * ) Notice: Subject to any disclaimer, the term of this patent is extended or adjusted under 35 U.S.C. 154(b) by 0 days.

(21) Appl. No.: 10/185,966

(22) Filed: Jun. 28, 2002

(65) Prior Publication Data

US 2003/0043880 A1 Mar. 6, 2003

(30) Foreign Application Priority Data

Jul. 4, 2001 (GB) .............................................. 0116354

(51) Int. Cl.⁷ ........................ G01K 11/22; G01K 17/00; G01K 13/00; G01H 5/00
(52) U.S. Cl. ........................ 374/32; 374/117; 374/118; 374/119; 73/597
(58) Field of Search ........................ 374/117–119, 142, 374/148, 31–33; 73/24.01, 25.01, 587, 597, 645, 170.12, 170.13

(56) References Cited

U.S. PATENT DOCUMENTS

| | | | | |
|---|---|---|---|---|
| 2,582,232 A | * | 1/1952 | Cesaro | |
| 3,600,515 A | * | 8/1971 | Carpenter | |
| 4,255,971 A | * | 3/1981 | Rosencwaig | |
| 4,372,149 A | | 2/1983 | Zharov | |
| 4,408,478 A | | 10/1983 | Bechthold et al. | |
| 4,578,584 A | * | 3/1986 | Baumann et al. | |
| 4,679,946 A | * | 7/1987 | Rosencwaig et al. | |
| 4,682,897 A | * | 7/1987 | Saito et al. | |
| 4,984,903 A | * | 1/1991 | Sweeney | |
| 5,141,331 A | * | 8/1992 | Oehler et al. | |
| 5,587,532 A | * | 12/1996 | Rose | 73/579 |
| 5,596,146 A | * | 1/1997 | Waller et al. | 73/590 |
| 5,657,754 A | * | 8/1997 | Rosencwaig | 128/633 |
| 5,998,681 A | * | 12/1999 | Rojey | 585/15 |
| 6,271,921 B1 | * | 8/2001 | Maris et al. | 356/432 |
| 6,378,372 B1 | * | 4/2002 | Karr | |
| 6,444,474 B1 | * | 9/2002 | Thomas et al. | |
| 6,449,370 B1 | * | 9/2002 | Yasuno et al. | |
| 2002/0006560 A1 | * | 1/2002 | van der Schaar et al. | 430/22 |
| 2002/0105999 A1 | * | 8/2002 | Wallen et al. | |
| 2003/0131787 A1 | * | 7/2003 | Linares et al. | 117/93 |

FOREIGN PATENT DOCUMENTS

| | | | | |
|---|---|---|---|---|
| AU | 000646576 | * | 1/1993 | ........... G01K/11/24 |
| DE | 3707622 | | 9/1988 | |
| EP | 1 205 748 | | 8/2001 | |
| JP | 3611134639 A | * | 6/1980 | ................. 374/117 |
| JP | 402176434 A | * | 7/1990 | ........... G01K/11/24 |
| SU | 769356 A | * | 10/1980 | ............. G01J/5/10 |

* cited by examiner

Primary Examiner—Gail Verbitsky
(74) Attorney, Agent, or Firm—Royal N. Ronning, Jr.; Yonggang Ji; Stephen G. Ryan

(57) ABSTRACT

The present invention relates to a method, a measuring cell and a system for measuring very small heat changes in a sample. The system comprises a measuring cell 16 for containing the sample during the measurement process, at least one electromagnetic radiation unit 14 for radiating one or several samples with modulated monochromatic or polychromatic radiation 46 inside said measuring cell 16. Said measuring cell 16 comprises at least one acoustic transducer 22 for generating a first output signal V(t) and at least one heat measuring device 24 for generating a second output signal T(t). Both signals are connectable to a combining unit 18 that generates an information signal by means of a reference signal f(t). Said information signal is connectable to a signal processing unit 20 for determining at least one relevant reaction parameter as a function of the measured heat change.

10 Claims, 8 Drawing Sheets

| Signal | Modulation | Phase | |
|---|---|---|---|
| $r(t)$ | $m_n^r$ | | |
| $S(t)$ | $m_a^s = \dfrac{k}{\sqrt{k^2+\omega_n^2}} m_n^r$ | $\Phi_a^s$ | |
| $T(t)$ | $m_a^T = \dfrac{k}{\sqrt{k^2+\omega_n^2}} \cdot \dfrac{k_e}{\sqrt{k_e^2+\omega_n^2}} m_n^r$ | $\Phi_n^T = \Phi_n^f - \theta_n^{(1)} - \theta_n^{(2)}$ | $tg(\theta_n^{(1)}) = \dfrac{\omega_n}{k}$ $tg(\theta_a^{(2)}) = \dfrac{\omega_n}{k_e}$ |
| $V(t)$ | $m_n^V = \dfrac{k}{\sqrt{k^2+\omega_n^2}} \cdot \dfrac{k_e}{\sqrt{k_e^2+\omega_n^2}} R_n m_n^r$ with $R_n = \dfrac{v^2}{\sqrt{(v^2-\omega_n^2)^2 + 4 \dfrac{\omega_n^2}{\tau_0^2}}}$ | $\Phi_a^V = \Phi_n^f - \theta_n^{(1)} - \theta_n^{(2)} - \theta_n^{(3)} - \psi$ | $tg(\theta_n^{(3)}) = \dfrac{2\omega_n}{\tau_0(v^2-\omega_n^2)}$ $\psi_n = \omega_n \dfrac{r_0}{v_0}$ |
| $C(t)$ | $m_a^f = \dfrac{k}{\sqrt{k^2+\omega_n^2}} \cdot \dfrac{k_e}{\sqrt{k_e^2+\omega_n^2}} R_a \dfrac{\sqrt{Z^2 R_a^2 + a^2 + 2Z R_a a \cos(\Phi_a^V - \Phi_v^T - \Delta\varphi)}}{(Z+a)} m_n^r$ | $tg(\Phi_v) = \dfrac{Z R_a \sin\Phi_a^V + a\sin(\Phi_a^T + \Delta\varphi)}{Z R_n \cos\Phi_a^V + a\cos(\Phi_a^T + \Delta\varphi)}$ with $Z = \dfrac{A}{v^2}$ | |

Table 1: Modulation and phase shift of the different signal with respect to the excitation light

Fig. 8

METHOD, A MEASURING CELL AND A SYSTEM FOR MEASURING VERY SMALL HEAT CHANGES IN A SAMPLE

TECHNICAL FIELD

The invention relates to the measurement of heat changes in samples. More specifically, the invention relates to a method, a measuring cell and a system for measuring very small heat changes in a sample.

BACKGROUND OF THE INVENTION

Thermodynamic data can be obtained from biological reactions by using a variety of devices. Such devices can include thermocouples, thermopiles etc.

Photoacoustic Calorimetry has been used in a wide range of different fields. Here follows some examples:

Phase transitions, Photoreaction dynamics, energetics of reactive intermediates;
Thermochemical and kinetic properties of reactive intermediates;
Information regarding inter/intra molecular reactions;
Bond dissociation enthalpies;
pKa estimations;
Key reaction parameters in important biological processes;
Radiationless decay processes in photophysical processes
Probing energetics and dynamics of fast chemical and biochemical reactions.

The list shall not be regarded as exhaustive. A number of articles about photoacoustic calometry and its different applications have been published. In an article by S. E. Braslavsky and G. E. Heibel in Chemical Review, 1992, pp. 1381–1410, the authors have carried out a review of the use of photoacoustic calorimetry for phase transitions, photoreaction dynamics and the energetics of reactive intermediates. In another article, a study was made of the thermochemical and kinetic properties of reactive intermediates of proteins using photoacoustic calometry(M. A McLean, C. Di Primo, E. Deprez, G. H. B. Hoa and S. A. Sligar, Methods in Enzymology, 295, 1998, pp. 316–330). Examples given are myoglobin and cytochrome P450cam. The authors, R. M. Borges dos Santos, A. L. C. Lagoa and J. A. M. Simoes, of an article in Journal of Chemical Thermodynamics, 31, 1999, pp. 1483–1510, describe in said article how photoacoustic calorimetry is used as a tool for high precision thermochemistry studies of transient species i.e. the reaction of phenol with di-tert-butyl peroxide. In Biophysical Journal, 79, 2000, pp. 2714–2721, an article by S. Abbruzzetti, C. Viappiani, L. J. Libertini and J. R. Small present a study of pKa measurements and the kinetics of reaction of acetate, glutamate and poly-I-glutamatic acid. The technique was applied to the quenching of the benzbphenone triplet states by dienes and the Norrish type II photoreaction of valerophenone and described by J. E. Rudski, J. L. Goodman and K. S. Peters in Journal of American Chemical Society, 107, 1985, p.7849. A paper by Kevin S. Peters and Gary J. Snyder (Science, 241, 1988, pp. 1053–1057, describes the measurement of the dynamics of enthalpy changes on the time scale of nanoseconds to microseconds for reactions initiated by the absorption of light. The method was applied to a variety of biochemical, organic and organometallic reactions.

A combined photoacoustic differential scanning calorimeter (PA-DSC) cell and an experimental set-up is known from an article by Ts. Vassilev et al.: "Combined photoacoustic differential scanning calorimeter cell: Application to phase transitions.", Applied Physics A 61, (1995), pp. 129–134. The combined PA-DSC cell consists of a conventional DSC unit adapted for variable temperature studies. This is accomplished in a way that allows to perform PA and DSC measurements simultaneously and separately. FIG. 1 in the article presents the construction of the cell. It is mounted on a conventional DSC chamber at the place of the DSC cover, thus utilising the heating and cooling capabilities of the DSC instrument. The cell consists of a sample chamber and a microphone chamber. A schematic diagram of the experimental set-up is illustrated in the article's FIG. 2.

A similar experimental set-up is also earlier known from an article by Tsvetan G. Vassilev: "A combined photoacoustic DSC for simultaneous temperature modulated measurements: does it really work?", Thermochimica Acta 330 (1999), pp.145–154. The experimental setup is illustrated in the article's FIG. 1.

SUMMARY OF INVENTION

The main problem in trying to obtain thermodynamic data from biological reactions is that prior art devices require the use of relatively large quantities of sample in order that meaningful results can be obtained.

It would therefore be beneficial to use a technique or device which provided some sort of signal amplification to allow the extraction of meaningful thermodynamic information from relatively small sample sizes.

The following invention describes the processes that could be used to combine the output signals derived from the microphone used in photoacoustic spectroscopy with the signal from a heat measuring device.

In short, the invention comprises a measuring cell for containing the sample during the measurement process. An electromagnetic radiation unit radiates one or several samples with modulated monochromatic or polychromatic radiation inside said measuring cell. The measuring cell comprises at least one acoustic transducer generating a first output signal and at least one heat measuring device generating a second output signal. Both output signals are connectable to a combining unit that can generate a combined output signal that can be sent to a signal processing unit.

In more detail, the present invention relates to a method according to claim 1 for measuring very small heat changes in at least one sample and determining reaction parameters. The method comprises the following steps:

modulating monochromatic or polychromatic electromagnetic radiation to excite a sample;
detecting the generated acoustic wave by the use of at least one acoustic transducer able to generate a first output signal in proportion to the heat change of the sample;
detecting a thermal wave by the use of at least one heat measuring device able to generate second output signal in proportion to the heat change of the sample;
generating at least one information signal by combining the first and the second output signals with a reference signal;
processing at least one of the information signals for determining the relevant reaction parameters.

Further, the present invention relates to a measuring cell according to claim 5 for measuring very small heat changes in at least one sample, which is/are radiated with modulated monochromatic/polychromatic electromagnetic radiation.

Said measuring cell comprises at least one acoustic transducer able to generate a first output signal in proportion to the heat change of the sample, and at least one heat measuring device able to be positioned in contact with the sample, said measuring device being able to generate a second output signal in proportion to the heat change of the sample. The transducer and heat measuring device are arranged in the same main body.

Further more, the present invention relates to a system according to claim 11 for measuring very small heat changes in at least one sample and determining reaction parameters. Said system comprises a measuring cell for containing the sample during the measurement process, at least one electromagnetic radiation unit for radiating one or several samples with modulated radiation inside said measuring cell. Said measuring cell comprises at least one acoustic transducer able to generate a first output signal and at least one heat measuring device able to generate a second output signal, which signals and a reference signal are input signals to a combining unit able to generate from said signals an information signal that is connected to a signal processing unit for determining the relevant reaction parameters.

The main advantage of this combination of generated signals is the signal amplification.

The other advantage of photoacoustic spectroscopy is that it is a modulated technique. Therefore, it is very sensitive for the measurement of a small AC signal in a large DC background.

BRIEF DESCRIPTION OF THE DRAWINGS

FIG. 8 contains a table, Table 1, of mathematical solutions to different equations discussed in the following description.

The same reference numbers are used for corresponding elements in FIGS. 1–7.

DETAILED DESCRIPTION OF THE INVENTION

Figure 1:
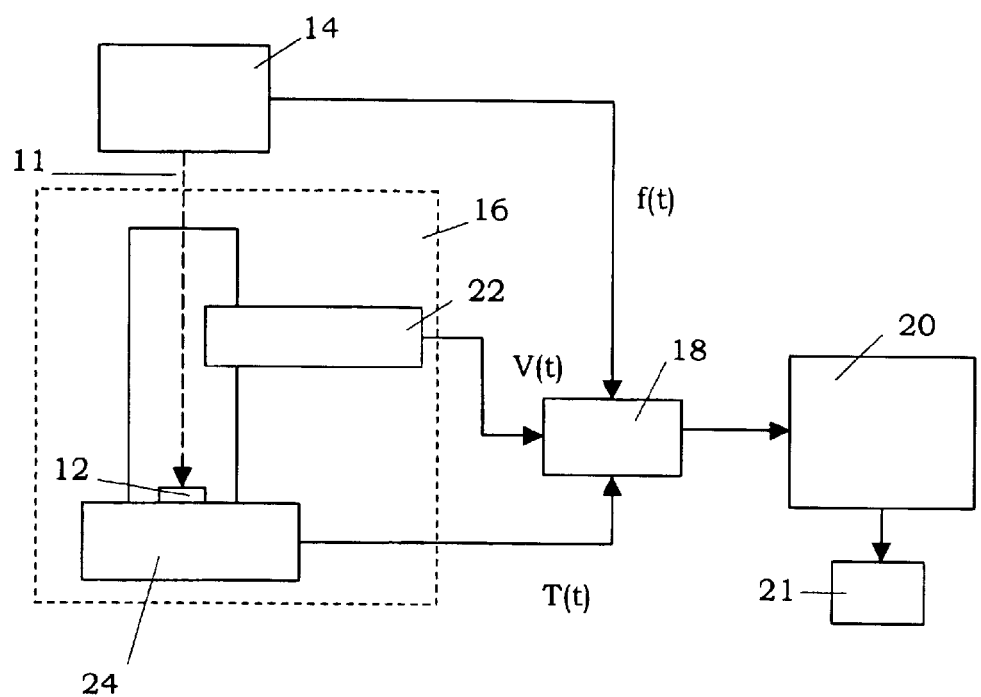
FIG. 1 is a block diagram illustrating an embodiment of the invented system.

FIG. 1 is a block diagram illustrating schematically a system 10 for measuring very small heat changes in at least one sample 12. The system 10 comprises an electromagnetic radiation unit 14, a measuring cell 16, a combining unit 18, a signal processing unit 20 and an output device 21.

The electromagnetic radiation unit 14 can radiate one or several samples 12 with modulated monochromatic or polychromatic radiation 11 inside a measuring cell 16 during the measurement process. The electromagnetic radiation unit 14 also generates a reference signal f(t) that is sent to a combining unit 18. The measuring cell 16 comprises at least one acoustic transducer 22 that generates a first output signal V(t) and at least one heat measuring device 24 that generates a second output signal T(t), said signals being connected to the combining unit 18 for combination with reference signal f(t) in order to generate at least one information signal that is transmitted to a signal processing unit 20 for further analysis by use of processors and appropriate software. The result of the analysis and measurement can be presented by means of an output device 21, such as a printer or a display.

In short, the method for measuring very small heat changes in a sample, according to the invention, comprises the following steps:

modulating a sample with monochromatic or polychromatic electromagnetic radiation;

detecting an acoustic wave by use of at least one acoustic transducer generating a first output signal in proportion to the heat change of the sample;

detecting a thermal wave by use of at least one heat measuring device generating a second output signal in proportion to the heat change of the sample;

generating an information signal by combining the first and the second output signals with a reference signal;

processing said information signal for determining a reaction rate constant k as a function of the measured heat change.

The key feature of the proposed instrument is that it will combine the photoacoustic measurement with a conventional calorimetric measurement involving measuring heat changes by the quantitation of voltage fluctuations by use of the heat measuring device. To achieve this feature the present, the newly invented design of a measuring cell 16 for this kind of system is needed. Such a cell is hereafter called a photoacoustic cell 16.

Figure 2:
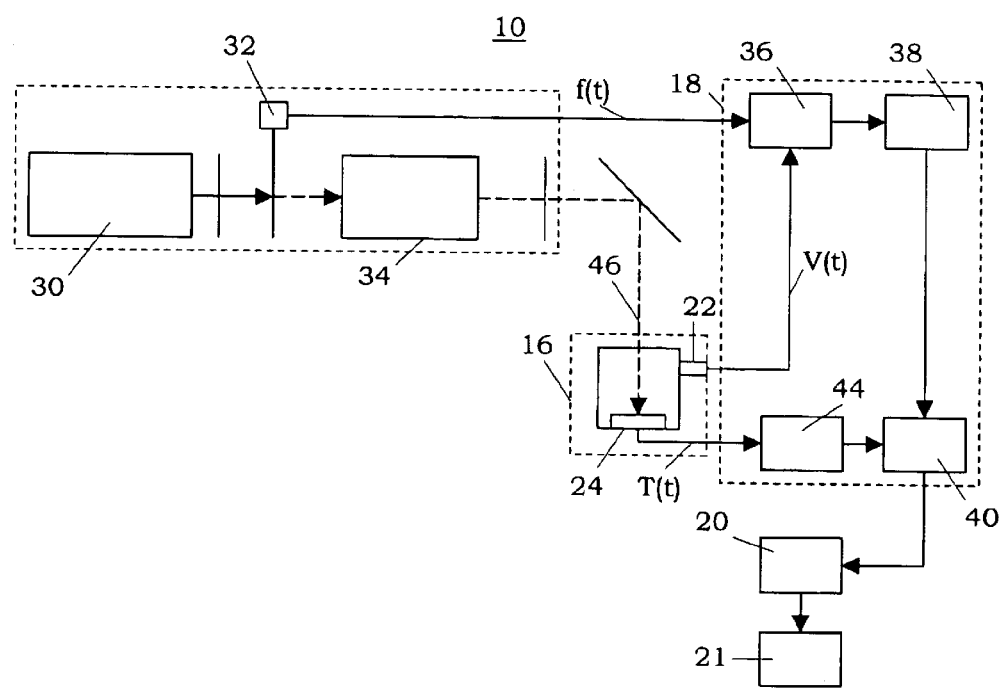
FIG. 2 is a more detailed embodiment of the invented system and its different units.

The system and its different components will now be described in more detail with reference to FIG. 2.

This embodiment of the invented system comprises light source 30, chopper 32, wavelength selection device 34, photoacoustic cell (measuring cell) 16, temperature sensor 24, microphone 22, first combining element 36, such as a lock-in amplifier, analogue-to-digital converter 38 (if needed), second combining element 40, signal-processing unit 20, such as a personal computer, and output device 21.

The electromagnetic radiation unit 14 comprises a light source 30 that can be a laser, a polychromatic light source such as a xenon arc, tungsten filament or mercury lamp, or a polychromatic light source with a wavelength selection device 34 such as a monochromator or an optical filter. The light is modulated either with a pulsed laser or with a mechanical chopper 32. Light is focussed onto a tilted mirror via a lens (not shown). The light is then focussed via another lens (not shown) onto the sample inside a photoacoustic cell 16.

Chopped monochromatic light 46 is focused onto the sample placed on the temperature sensor chip 24 in the base of the photoacoustic cell 16. The resultant temperature pulse is measured with the aid of the microphone 22. The signal V(t) from the microphone 22 is passed via a pre-amplifier (not shown) to a first combining element 36, preferably a lock-in amplifier. A signal from the opto-mechanical chopper 32 is also passed to the lock-in amplifier 36. This allows the relative phase of the two signals to be modified to provide the optimum signal. The output signal from the lock-in amplifier 36 is connected to a second combining element 40, which could be implemented as a lock-in amplifier or a data storage. The output signal from the temperature sensor chip 24 is also passed into the second combining element 40, via a pre-amplifier 44, for combining the signals.

Depending on the type of second combining element 40 and lock-in amplifier 36 used, it might be necessary to use an analogue-to-digital converter 38.

The photoacoustic cell 16 has a microphone 22 for measuring the photoacoustic signal V(t) and a calorimetric chip for measuring temperature T(t). The output signal from the microphone V(t) and the reference signal f(t) from the chopper (Perkin Elmer Sigrec 197 precision light chopper) are fed into a lock-in amplifier (Perkin Elmer Instruments Sigrec 7280 wide bandwidth dual phase DSP lock-in amplifier).

Output from the lock-in amplifier 36 and the other signal (from the calorimetric chip 24 or optical chopper 32) can then be processed in one of two ways viz. By passing each signal through a digital-to-analogue converter 38 before manipulating the data on the computer 42 or by combining both signals electronically before passing the combined signal through the digital-to-analogue converter 38 and into the signal-processing unit 20.

Output from the lock-in amplifier 36 is transferred to a data acquisition unit before being manipulated by a signal-processing unit 20. The result of the analysis and measurement can be presented by means of an output device 21, which could be implemented as a printer or a display.

Different possible signal handling combinations in a system according to the invention are possible:

(1) feed microphone signal V(t) and reference signal f(t) from chopper 32 into a lock-in amplifier 36b;

(2) feed reference signal f(t) plus calorimetric chip signal T(t) into lock-in amplifier 36a;

(3) add microphone signal V(t) and calorimetric chip signal T(t) electronically before feeding into lock-in amplifier 36 with reference signal f(t) from the chopper 32;

(4) multiply microphone signal V(t) and calorimetric chip signal T(t) electronically before feeding into lock-in amplifier 36 with reference signal f(t) from the chopper 32.

Besides the temperature sensor, different combinations of light source, chopper and acoustic transducer/microphone elements are possible in a system according to the invention. Such a combination may comprise:

1. a polychromatic light source, an optical chopper and a condenser microphone; or
2. a polychromatic light source, a monochromator, an optical chopper and a condenser microphone; or
3. a pulsed laser and a piezoelectric transducer (no optical chopper is required); or
4. a tuneable pulsed laser and a piezoelectric transducer (no optical chopper is required); or
5. a CW laser with an optical chopper and a microphone that can be piezoelectric or condenser.

In another embodiment of the present invention a CW laser/chopper or pulsed laser is used for stimulating samples on an array in the photoacoustic cell. Either the laser beam could be moved to scan the array or the array itself could be moved. Either method would result in one sample being measured at any one time.

If the laser beam is focused onto a dichroic mirror, the beam could be used to stimulate a sample in a separate device or devices, thus enabling further but different signals to be generated e.g. fluorescence, uv/visible/infra red absorption, etc.

A microphone that can be used is a ½ inch Bruel & Kjaer type 4176 condenser microphone fitted with a Bruel & Kjaer model 2669-B ½ inch microphone pre-amplifier and powered by an appropriate power supply.

The output signal from the microphone and the reference signal from the chopper (Perkin Elmer Sigrec 197 precision light chopper) are fed into a lock-in amplifier (Perkin Elmer Instruments Sigrec 7280 wide bandwidth dual phase DSP lock-in amplifier).

The type of transducer required is dependent upon the lifetime of the reaction under consideration. If the lifetime is of the order of a few milliseconds or slower, a normal microphone transducer can be used. If the lifetime is faster, a piezoelectric transducer has to be used.

Again, modulating or chopping frequencies are also dependent upon the lifetime of the reaction under consideration. Slower reactions require a chopping frequency of 10 Hz to approximately 1 kHz. Faster reactions require a chopping frequency greater than 1 kHz.

In order to give a better understanding of the inventive concept of the present invention an explanation of the mathematical relations of the physical parameters is discussed in the following.

The following mathematical representation is used:

The reference signal f(t) is similar to the excitation light. This is a periodic function of time, with a typical frequency between 10 Hz and 1 kHz. The frequency of the excitation, which is defined by the frequency of the chopper and which is the same as the frequency of the reference signal, is called the modulation frequency.

The signal from the V(t) can represent the voltage generated by the microphone. This is a periodic function of time. The frequency of that signal is similar to the modulation frequency of the excitation light, i.e. it has a typical frequency between 10 Hz and 1 kHz.

The signal from the temperature sensor is T(t) and can represent the voltage generated by the sensor. It is a periodic function of time. The frequency of that signal is similar to the modulation frequency of the excitation light, i.e. it has a typical frequency between 10 Hz and 1 kHz.

Thus, the three electrical signals are periodic functions varying in time and the frequency of the three signals is similar and is equal to the modulation frequency.

The information of the biochemical reaction taking place in the photoacoustic cell is included in the signals V(t) and T(t).

$C^+(t)$ is some combination of T(t) and V(t). It is a periodic function of time.

The flash of light is used to initiate a reaction (e.g. photochemical reaction, temperature rise, . . . ). In a first approximation, the reaction is supposed to be a first order reaction. Therefore, the rate of substrate S consumption, can be described by the following differential equation:

$$\frac{dS(t)}{dt} = -k \cdot S(t) + f(t) \cdot \phi \qquad \text{Eq. 1.}$$

k is the reaction rate constant, which is the parameter to be measured in the following described example. $\phi$ is the quantum yield, which is the proportionality constant relating the light intensity to the concentration of substrate generated by this light intensity.

Because the excitation light is a periodical signal, the substrate concentration will vary periodically. The substrate concentration can be described by a Fourier series:

$$S(t) = A_0^s + \sum_{n=1}^{\infty} B_n^s \cdot \cos(\omega_n t + \Phi_n - \theta_n^1)$$ Eq. 2

The modulation $m_n^s$ of the concentration is defined as:

$$m_n^s = \frac{B_n^s}{A_0^s}$$ Eq. 3

As stated above, the excitation light is a periodic function of time. In order for the analysis to be general, this function can have any shape, by amplitude or period, provided it is a periodical function. Any periodical function can be described as a sum of cosine functions, using the development in a Fourier series. Therefore, the function f(t) can be described by:

$$f(t) = A_0^f + \sum_{n=1}^{\infty} B_n^f \cdot \cos(\omega_n \cdot t + \Phi_n^f)$$ Eq. 4

$$\omega_n = n \cdot \frac{2 \cdot \pi}{T} : \omega_1$$

is the fundamental frequency, $\omega_n$ are the harmonics.

T: is the period of the periodic signal $A_0^f$ and $B_n^f$: are the Fourier coefficients. They will be different for different functions. Each harmonic n has a different amplitude $B_n^f$.

$\Phi_n^f$: is the phase of the harmonic n.

The modulation $m_n^f$ of light is defined as:

$$m_n^f = \frac{B_n^f}{A_0^f}$$ Eq. 5

By inserting Eq. 4 and Eq. 2 into Eq. 1, it is possible to determine the phase shift $\Phi_n^f$ and modulation $m_n^f$ of the S(t) from the modulation and phase shift of f(t). The relation of the concentration modulation and the phase with the reaction parameters is given in the table of FIG. 8. The concentration varies in a periodic manner. The harmonics of the Fourier series are demodulated and phase shifted with the respect to the corresponding harmonics of the excitation light.

The reaction generates an amount of heat. The conversion of one mole of substrate into product generates a heat $\Delta H$. This heat will be dissipated in two ways:

1. Dissipation into the environment. The rate of heat dissipation is proportional to the temperature difference between the solution and the environment. The proportionality constant is called $k_c$.
2. Increase of the solution temperature. There is a mass m of solution with a specific heat $c_p$.

Therefore the rate of heat change is given by:

$$\frac{dT(t)}{dt} = -k_c \cdot T(t) + k_H \cdot k \cdot S(t)$$ Eq. 6 wherein $$k_H = \frac{\Delta H}{m \cdot c_p}.$$

The temperature is a periodic function of time that can be described by a Fourier series:

$$T(t) = A_0^T + \sum_{n=1}^{\infty} B_n^T \cdot \cos(\omega_n \cdot t - \phi_n^T)$$ Eq. 7

The modulation $m_n^T$ of the concentration is defined as:

$$m_n^T = \frac{B_n^T}{A_0^T}$$ Eq. 8

By inserting Eq. 7 and Eq. 2 into Eq. 6, it is possible to determine the phase shift $\Phi_n$ and modulation $m_n^T$ of the T(t) from the modulation and phase shift of f(t). The relation of the temperature modulation and the phase with the reaction parameters is given in the table of FIG. 8. The temperature varies in a periodic manner. The harmonics of the Fourier series are demodulated and phase shifted with respect to the corresponding harmonics of the excitation light.

The variation of temperature of the reaction solution will result in a variation of pressure close to the reaction solution. The variation of pressure will be transmitted to the microphone as a sound wave. This sound wave will induce a vibration in the microphone membrane. The voltage coming out of the microphone is proportional to the amplitude of the vibration of the microphone membrane. The vibration is described by a standard wave equation:

$$\frac{d^2V}{dt^2} + \frac{2}{\tau_0} \cdot \frac{dV}{dt} + v^2 \cdot V = A' \cdot A'' \cdot T\left(t - \frac{r_0}{v_0}\right)$$ Eq. 9 wherein,

V(t): the voltage generated by the microphone.

$\tau_0$: damping time constant of the microphone membrane.

$\upsilon$: Intrinsic vibration frequency of the microphone membrane.

A': Proportionality constant between the pressure applied on the microphone and the voltage generated by the microphone.

A'': Proportionality constant between the pressure and the temperature.

$r_0$: distance between the microphone and the place where the heat is generated.

$v_0$: speed of sound.

To simplify the notation, A is defined A=A',A''.

The voltage varies as a periodic function of the time that can be described as a Fourier series:

$$V(t) = A_0^V + \sum_{n=1}^{\infty} B_n^V \cdot \cos(\omega_n \cdot t - \phi_n^V)$$ Eq. 10

The modulation $m_n^V$ of the voltage is defined as:

$$m_n^V = \frac{B_n^V}{A_0^V} \quad \text{Eq. 11}$$

By inserting Eq. 10 and Eq. 7 into Eq. 9, it is possible to determine the phase shift $\Phi_n$ and modulation $m_n^V$ of the V(t) from the modulation and phase shift of f(t). The relation of the temperature modulation and the phase with the reaction parameters is given in the table of FIG. 8. The voltage varies in a periodic manner. The harmonics of the Fourier series are demodulated and phase shifted with respect to the corresponding harmonics of the excitation light.

The signal from the temperature sensor and the pressure sensor (microphone) are both electric signals. Both signals are represented by a variation of voltage as a function of time. It is therefore possible to combine the two signals. Different combinations can be used. We will only analyse here the addition of the two signals.

The summation signal $C^+(t)$ results from the addition of T(t) and V(t) signals:

$$C^+(t) = V(t) + \alpha \cdot T(t+\Delta\phi) \quad \text{Eq. 12}$$

Wherein $\alpha$ is an amplification constant and $\Delta\phi$ is the phase difference between V(t) and T(t) that is introduced before adding the signals. The $C^+(t)$ will vary as a periodic function of time that can be described as a Fourier series:

$$C^+(t) = A_0^+ + \sum_{n=1}^{\infty} B_n^+ \cdot \cos(\omega_n \cdot t - \phi_n^+) \quad \text{Eq. 13}$$

The modulation $m_n^+$ of the concentration is defined as a:

$$m_n^+ = \frac{B_n^+}{A_0^+} \quad \text{Eq. 14}$$

By inserting Eq. 7, Eq. 10 and Eq. 13 into Eq. 12, it is possible to determine the phase shift $\Phi_n$ and modulation $m_n^+$ of the $C^+(t)$ from the modulation and phase shift of f(t). The relation of the combination modulation and the phase with the reaction parameters is given in the table of FIG. 8. The summation signal varies in a periodic manner. The harmonics of the Fourier series are demodulated and phase shifted with respect to the corresponding harmonics of the excitation light.

A lock-in amplifier is used to measure the modulation and the phase of a signal when compared to a reference signal. X(t) denotes a general periodic signal. X(t) could be T(t), V(t) or $C^+(t)$ as defined above, or any other type of periodic signal. The lock-in amplifier introduces a phase shift $\Delta\phi_{LI}$ in the reference signal, multiplies the shifted reference f(t+$\Delta\phi_{LI}$) with the measured signal X(t) and then integrates the resulting time varying product. Mathematically, the effect of the lock-in amplifier can be described by:

$$L(\Delta\varphi_{LI}) = \int_{-\infty}^{\infty} f(t+\Delta\varphi_{LI}) \cdot X(t) \cdot dt \quad \text{Eq. 15}$$

It should be noted that the signals entering into the lock-in amplifier are time varying signals. The signal coming out of the lock-in amplifier is a DC-voltage (i.e. independent of time) that depends on the phase shift $\Delta\phi_{LI}$. The reference f(t) and the signal X(t) can each be described as a Fourier series of cosine functions:

$$f(t+\Delta\varphi_{LI}) = A_0^f + \sum_{n=1}^{\infty} B_n^f \cdot \cos(\omega_n \cdot t + \Phi_n^f + \Delta\varphi_{LI}) \quad \text{Eq. 16}$$

$$X(t) = A_0^X + \sum_{n=1}^{\infty} B_n^X \cdot \cos(\omega_n \cdot t + \Phi_n^X)$$

T(t) and V(t) contain the information on the biochemical reaction taking place in the photoacoustic cell. Briefly, the information about the biochemical reaction, i.e. its kinetics rate constant k, is "encoded" in the phase shift $\Phi(\omega)$ and the demodulation $m(\omega)$ between the input and the output signal, i.e. between T(t) and f(t) or between V(t) and f(t).

The signal can be represented by either Eq. 7, Eq. 10 or Eq. 13. Inserting Eq. 16 into Eq. 15, one finds that the resulting signal coming out of the lock-in amplifier is a periodic function of the phase shift $\Delta\phi_{LI}$:

$$L(\Delta\varphi_{LI}) = A_0^L + B_0^L \cdot \cos(\Delta\varphi_{LI} + \Delta\Phi) \quad \text{Eq. 17}$$

It can be shown that the phase shift $\Delta\Phi$ is defined by:

$$tg(\Delta\Phi) = \frac{\sum_{n=1}^{\infty} m_n^f \cdot m_n^X \cdot \sin(\Delta\Phi_n)}{\sum_{n=1}^{\infty} m_n^f \cdot m_n^X \cdot \cos(\Delta\Phi_n)} \quad \text{Eq. 18}$$

with $\Delta\Phi_n = \Phi_n^f - \Phi_n^X$.

The $m_n^X$'s represent the modulation of the different harmonics of the reference and the measurement signal, as defined previously (see Eq. 8, Eq. 11 or Eq. 14). The modulation $m^{LI}$ of the signal generated by the lock-in amplifier is defined as:

$$m^{LI} = \frac{B_o^{LI}}{A_o^{LI}} \quad \text{Eq. 19}$$

It can be shown that the modulation of the lock-in signal is related to the modulation of the reference and the measurement signal by the following equation:

$$m^{LI} = \frac{1}{2}\sqrt{\left(\sum_{n=1}^{\infty} m_n^X \cdot m_n^f \cdot \cos(\Delta\Phi_n)\right)^2 + \left(\sum_{n=1}^{\infty} m_n^X \cdot m_n^f \cdot \sin(\Delta\Phi_n)\right)^2} \quad \text{Eq. 20}$$

where the $m_n^X$'s are defined in FIG. 8 and the $m_n^S$'s are any of the modulations defined in FIG. 8.

Therefore, it is possible to extract the reactions parameters, e.g. k, from the modulation and phase shift of the signal coming out of the lock-in amplifier, by using Eq. 20 and Eq. 18 and the equations in FIG. 8.

The purpose of the signal analysis is therefore to extract the phase shift and the demodulation from the T(t) and V(t) signals. The phase shift and the demodulation are measured at different modulation frequencies. Three ways of extracting this information are suggested, namely:

1. Lock-in of V(t) and T(t) separately followed by combined data analysis.
2. Addition of V(t) and T(t), followed by lock-in followed by data analysis.
3. Multiplication of V(t) and T(t) followed by lock-in, followed by data analysis.

Each of these options is detailed in the following FIGS. 3–5.

Figure 3:
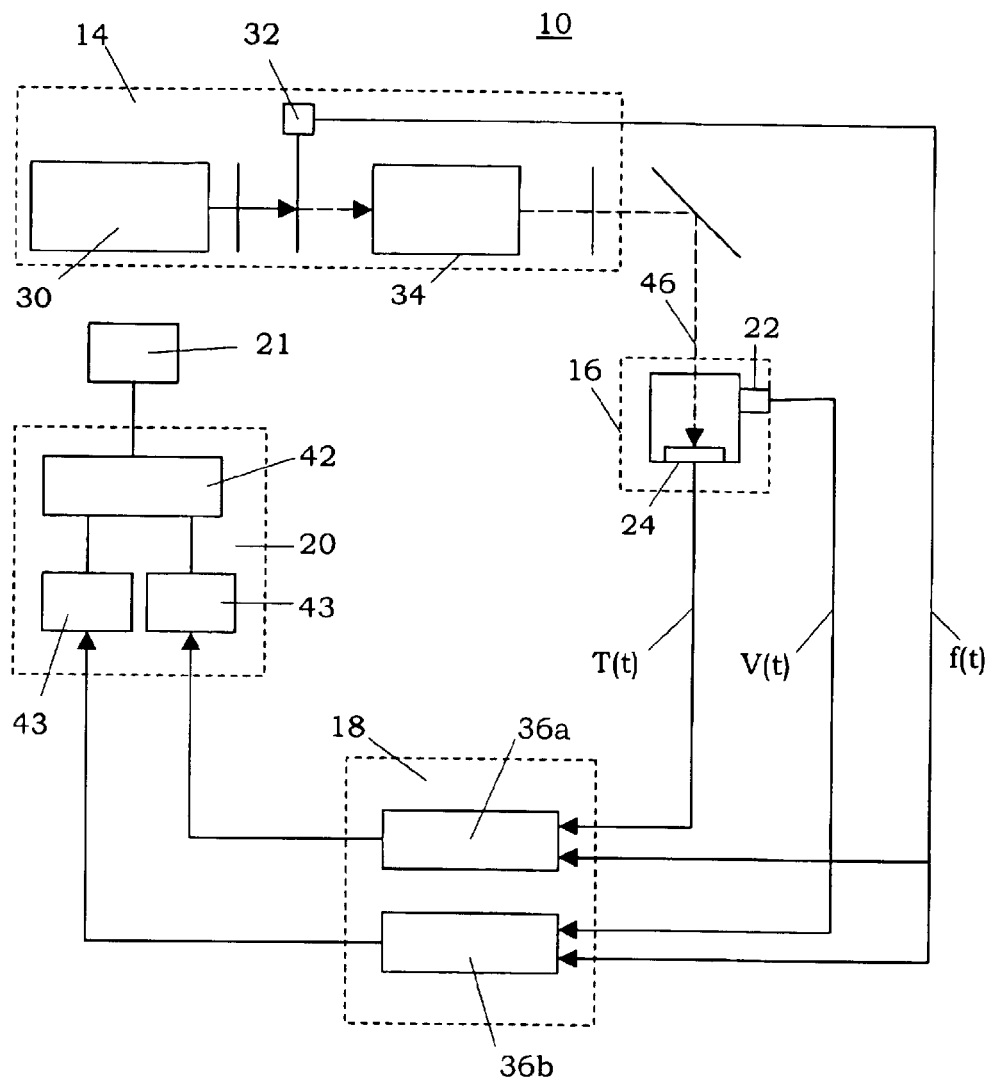
FIG. 3 is a block diagram that illustrates a preferred embodiment of an experimental system set-up according to the invention.

FIG. 3 illustrates a preferred embodiment of an experimental system set-up according to the invention for option 1. In this set-up, the T(t) and the V(t) signals are fed separately into different lock-in amplifiers, 36a and 36b, of a combining unit 18. Therefore, one extracts the m(ω) and Φ(ω) functions from each signal individually using two lock-in amplifiers 36a and 36b. The phase and demodulation are measured at different modulation frequencies ω in order to build the m(ω) and Φ(ω) curves. The system 10 according to this suggested embodiment of the invention comprises an above-described electromagnetic radiation unit 14 able to generate a reference signal f(t) corresponding to the excitation signal, a measuring cell 16 able to simultaneously generate a first output signal V(t) and a second output T(t). The system also comprises a combining unit 18 that is connected to a signal-processing unit 20, which is connected to an output device 21. The combining unit 18 comprises two lock-in amplifiers, 36a and 36b, in parallel. The first output signal V(t) from the measuring cell 16 and the reference signal f(t) are connected to lock-in amplifier 36b and the second output signal T(t) and the reference signal f(t) are connected to the lock-in amplifier 36a. The first lock-in amplifier, 36a, is able to generate a first information signal of the first output signal V(t) and the reference signal f(t), and the second lock-in amplifier, 36b, is able to generate a second information signal from the second output signal T(t) and the reference signal f(t). Both information signals are connected to the signal processing unit 20 as input signals for determining the relevant reaction parameters.

In this option, the information about the phase and modulation are extracted by the lock-in amplifiers 36a, 36b from each signal T(t) and V(t) separately. The information about the phase and the modulation are then fed into the signal processing unit 20 as information signals. The signal combination takes place in the computer 42, during the curve fitting. Hence, the combination of the information takes place by means of curve fitting software 43 in the computer 42. The parameter that is varied during the fit is k, the reaction rate constant (see equation Eq. 1.). The best fit gives the value of k. The value k and/or the result of the analysis and measurement can be presented by means of the output device 21. However, in this embodiment of the invention the parameter k is determined, but other relevant reaction parameters could also be determined by means of the invented system and method.

Figure 4:
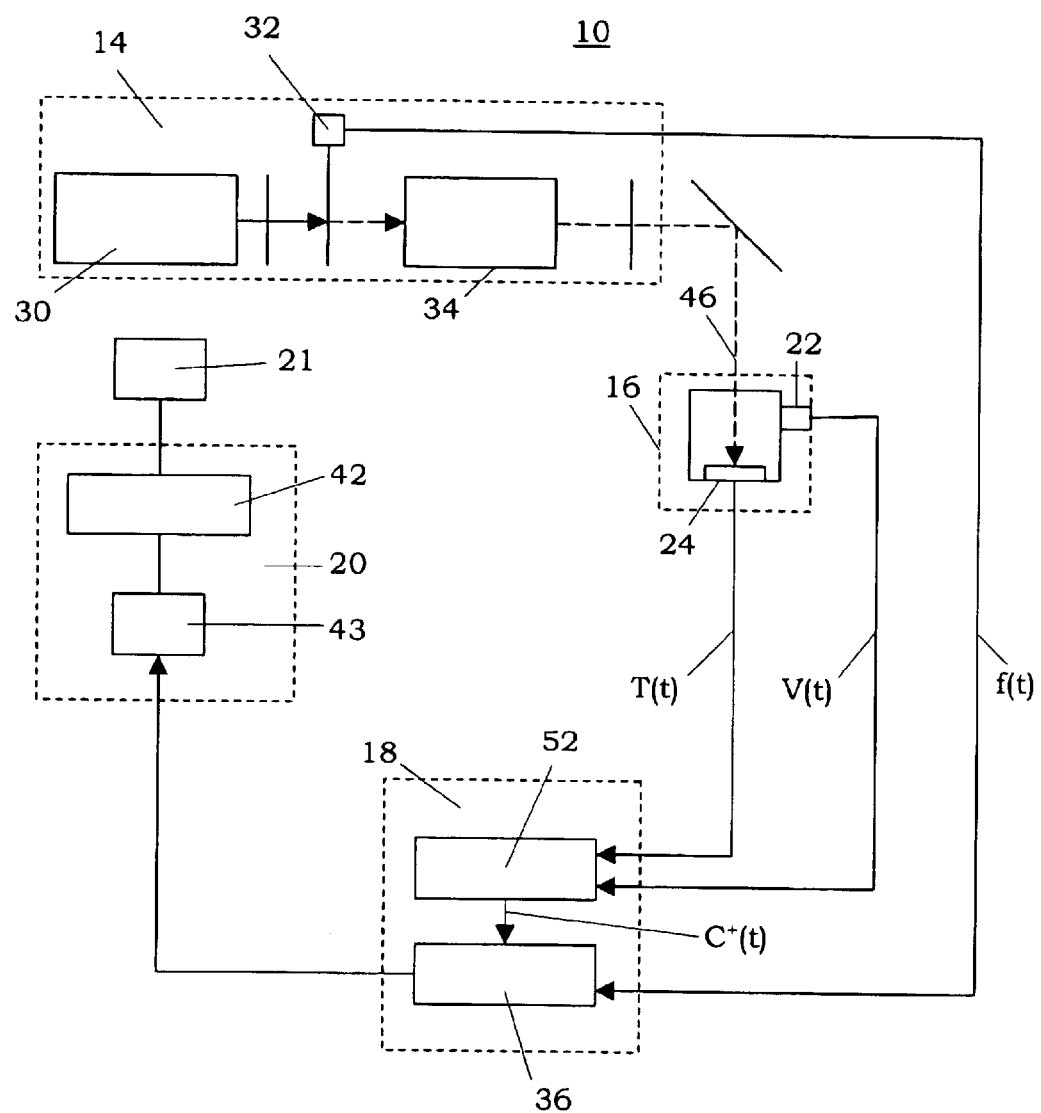
FIG. 4 is a block diagram that illustrates another preferred embodiment of an experimental system set-up according to the invention.

FIG. 4 illustrates another preferred embodiment of an experimental system set-up according to the invention. In this set-up according to option 2, the two signals, T(t) and V(t), are added together, electronically, to generate a new signal $C^+(t)$ that varies periodically with time. The frequency of the signal is similar to the modulation frequency ω. The system 10 according to this suggested embodiment of the invention comprises an above-described electromagnetic radiation unit 14 able to generate a reference signal f(t) corresponding to the excitation signal, a measuring cell 16 able to simultaneously generate a first output signal V(t) and a second output T(t). The system also comprises a combining unit 18 that is connected to a signal-processing unit 20, which is connected to an output device 21. The combining unit 18 comprises a signal adding module 52 and lock-in amplifier 36 that is connected to the output of the module 52. The first and second output signals from the measuring cell are connected to the module 52 and the reference signal is connected to the lock-in amplifier 36.

In this option, the combination of the information takes place in the combining unit 18 by means of an electronic module 52 that is placed before the lock-in amplifier 36. This signal $C^+(t)$ is fed into the lock-in amplifier 36 of the combining unit 18. The lock-in amplifier measures the phase shift $\Phi^+(t)$ and the demodulation $m^+(\omega)$ of the $C^+(t)$ signal with respect to the reference signal, which corresponds to the excitation signal f(t) from the chopper 32 of the electromagnetic radiation unit 14.

The lock-in amplifier 36 extracts the demodulation and the phase of the $C^+(t)$ for different modulation frequencies ω. The lock-in amplifier 36 produces an information signal that comprises the demodulation $m^+(\omega)$ and the phase $\Phi^+(\omega)$ information. The information is then fed into the signal processing unit 20. The information is processed by means of curve fitting software 43 in the computer 42. The parameter that is varied during the fit is k, the reaction rate constant (see equation Eq. 1.). The best fit gives the value of k. The value k and/or the result of the analysis and measurement can be presented by means of the output device 21. However, in this embodiment of the invention the parameter k is determined, but other relevant reaction parameters could also be determined by means of the invented system and method.

Figure 5:
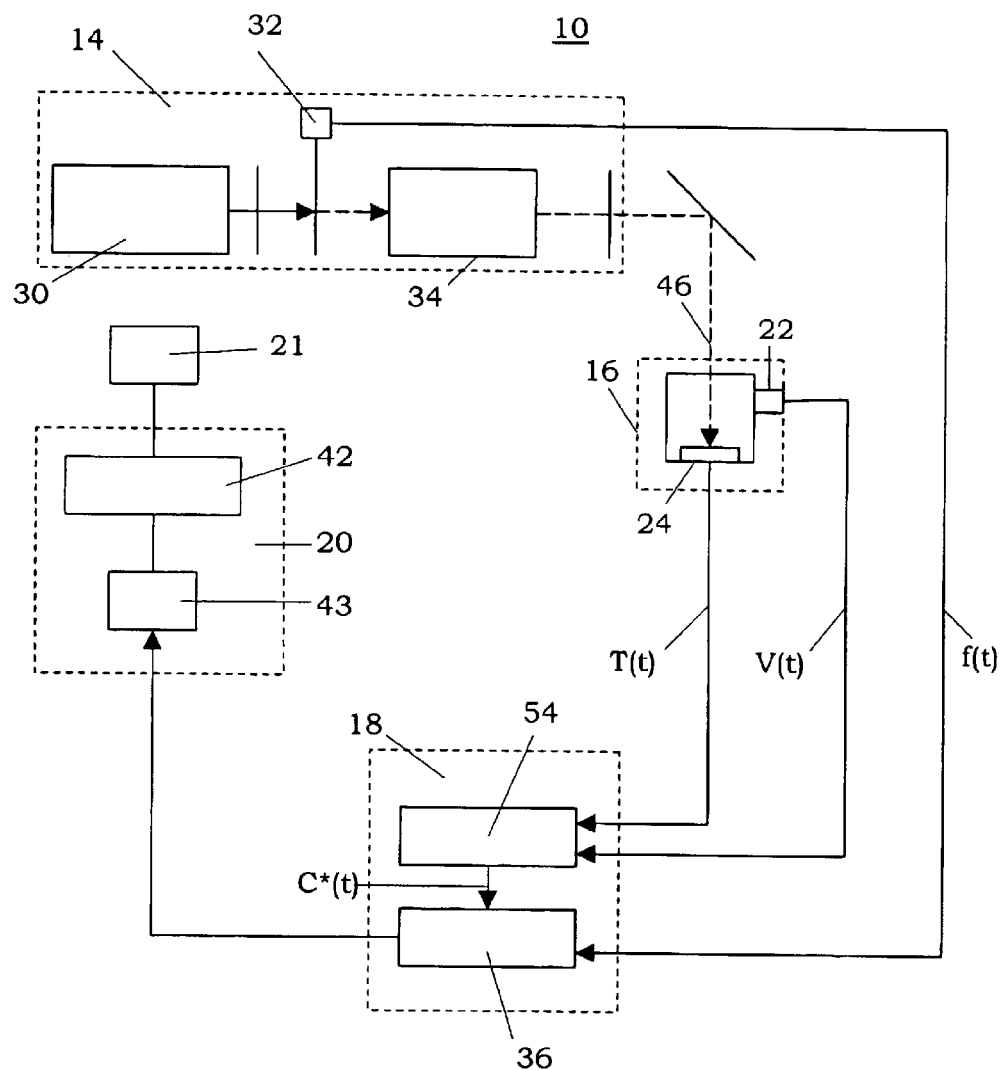
FIG. 5 is a block diagram that illustrates further one preferred embodiment of an experimental system set-up according to the invention.

FIG. 5 illustrates further one preferred embodiment of an experimental system set-up according to the invention. In this set-up for the option 3 combination, the two signals, T(t) and V(t), are multiplied together, electronically, to generate a new signal $C^*(t)$ that varies periodically with time at the modulation frequency ω. The system 10 according to this suggested embodiment of the invention comprises an above-described electromagnetic radiation unit 14 able to generate a reference signal f(t) corresponding to the excitation signal, a measuring cell 16 able to simultaneously generate a first output signal V(t) and a second output T(t). The system also comprises a combining unit 18 that is connected to a signal-processing unit 20, which is connected to an output device 21. The combining unit 18 comprises a signal multiplying module 54 and lock-in amplifier 36 that is connected to the output of the module 54. The first and second output signals from the measuring cell are connected to the module 54 and the reference signal is connected to the lock-in amplifier 36.

In this option, the combination of the signals takes place in the combining unit 18 by means of an electronic module 54 placed before the lock-in amplifier 36. This signal $C^*(t)$ is fed into the lock-in amplifier 36 of the combining unit 18. The lock-in amplifier 36 measures the phase shift $\Phi^*(t)$ and the demodulation $m^*(\omega)$ of the $C^*(t)$ signal with respect to the reference signal f(t), which corresponds to the excitation signal from the chopper 32 of the electromagnetic radiation unit 14.

The lock-in amplifier 36 extracts the demodulation $m^*(\omega)$ and the phase $\Phi^*(\omega)$ of the C(t) for different modulation frequencies ω. The lock-in amplifier 36 produces an information signal that comprises the demodulation $m^*(\omega)$ and phase $\Phi^*(\omega)$ information. The information is fed into the signal processing unit 20 and processed by means of curve fitting software 43 in the computer 42 of the signal processing unit 20. The parameter that is varied during the fit is k, the reaction rate constant (see equation Eq. 1.). The best fit gives the value of k. The value k and/or the result of the analysis and measurement can be presented by means of the output device 21. In this embodiment of the invention the parameter k is determined, but other relevant reaction parameters could also be determined by means of the invented system and method.

In the following the design of two embodiments of photoacoustic cells of a system in accordance with the present invention will be described.

The photoacoustic cell can be made from a variety of materials such as metal, glass or plastic.

Cell Design 1

Figure 6:
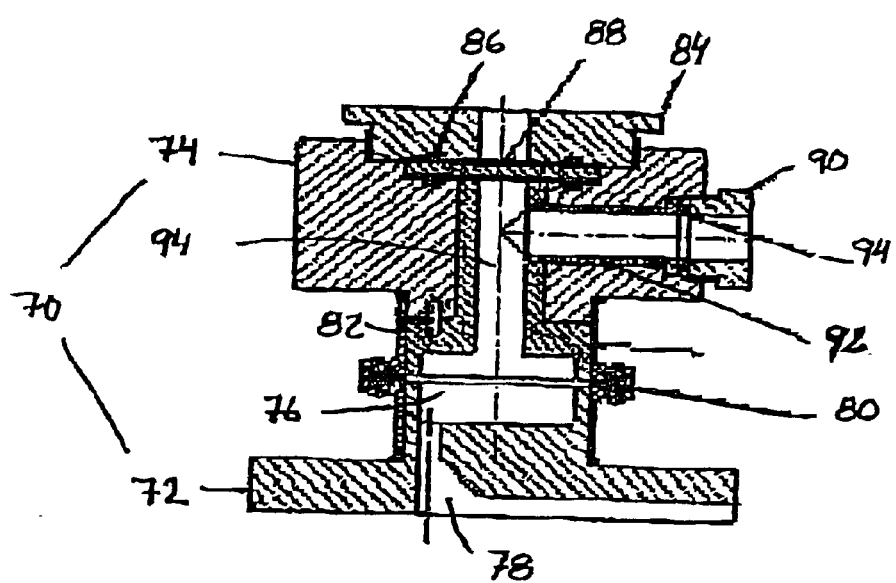
FIG. 6 shows an embodiment of a photoacoustic cell.

An embodiment of a photoacoustic cell is shown in FIG. 6. The main body 70 of the cell 16 is made in two parts, 72 and 74. A bottom part, the cell base 72, consists of a block with a measuring aperture 76 and a slot cut (not shown) that will hold a calorimetric chip (not shown), e.g. Xensor chip. The chip is mounted on an inverted cup (not shown) beneath which the amplification electronics are located. The cup is, preferably, designed to plug in place, thus allowing it to be easily removed. This also means that other types of detectors such as thermocouples, thermistors etc. could be used using the same type of inverted cup approach. Beneath the cup, in the cell base 72, a channel 78 has been cut to accommodate the wires from the electronics.

The bottom part 72 of the cell is clamped in place with the top part 74 of the cell by a clamp 80 and the join is made airtight using a rubber O-ring 82. The upper part 74 of the cell 16 consists of a block with two holes drilled at right angles to each other, the vertical excitation light channel 94 and the horizontal microphone insert 92. Both have screw caps 84, 90 and O-rings 86, 94b at one end. The top screw cap 84, also called the window retaining nut 84, is sealed by a window O-ring 86 fitted with a quartz sapphire window 88 or other suitable window, depending on the wavelength region of interest. The side screw cap 90, also called microphone retaining nut 90, is used to seal a microphone in place. The microphone can be slotted into the aperture 92, even called microphone insert 92, fairly easily if a ptfe liner is used.

Cell Design 2 (Isothermal)

Figure 7:
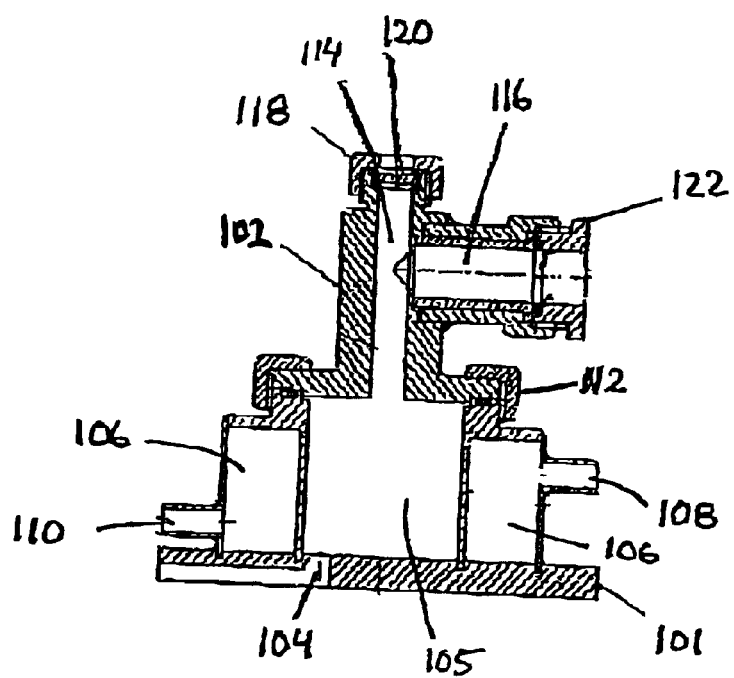
FIG. 7 reveals one further embodiment of a photoacoustic cell.

A further embodiment of a photoacoustic cell is illustrated in FIG. 7. The main body of this cell 16 is also made in two parts, 101 and 102. A bottom part 101 consists of a block with a measuring aperture 105 and a slot cut (not shown) that will hold a calorimetric chip, e.g. Xensor chip, which also is not shown. The chip is mounted on an inverted cup beneath which the amplification electronics are located. The cup is designed to plug in place, thus allowing it to be easily removed. This also means that other types of detectors such as thermocouples, thermistors etc. could be used using the same type of inverted cup approach. Beneath the cup, in the cell base 101, a channel 104 has been cut to accommodate the wires from the electronics.

The bottom part, or cell base, 101 of the cell 16 also has a temperature control water jacket 106 fitted, with an inlet 108 and outlet pipe 110 connection. These can be connected to a re-circulating water bath.

The bottom part 101 of the cell 16 is joined to the top part 102 by a screw cap, called a clamping nut 112, threaded arrangement and the join is made airtight using a rubber O-ring. An upper part 102 of the cell 16 consists of a stainless steel block with two holes, the vertical excitation light channel 114 and the horizontal microphone insert 116, drilled at right angles to each other. Both have screw caps and 'o' rings at one end. The top screw cap, the window retaining cap 118, is fitted with a quartz sapphire window 120 or other suitable window, depending on the wavelength region of interest. The side screw cap 122, also called microphone retaining nut, is used to seal a microphone in place. The microphone can be slotted into an aperture 116, even called the microphone insert, fairly easily due to the use of a ptfe liner.

The present invention is not limited to the above-described preferred embodiments. Various alternatives, modifications and equivalents may be used. Therefore, the above embodiments should not be taken as limiting the scope of the invention, which is defined by the appended claims.

What is claimed is:

1. A method for measuring heat changes in at least one sample and determining reaction parameters, comprising following steps:

modulating monochromatic or polychromatic electromagnetic radiation to excite a sample and generate an acoustic wave;

detecting the generated acoustic wave by the use of at least one acoustic transducer able to generate a first output signal (V(t)) in proportion to any heat change of the sample;

detecting a thermal wave by the use of at least one heat measuring device able to generate second output signal (T(t)) in proportion to any heat change of the sample;

generating at least one information signal by combining the first (V(t)) and the second (T(t)) output signals with a reference signal;

processing at least one of the information signals for determining the relevant reaction parameters.

2. The method of claim 1, wherein the information signal is generated by:

adding the first (V(t)) and the second (T(t)) output signals electronically to generate a combined signal; and feeding the combined signal and a reference signal (f(t)) into a lock-in amplifier (36).

3. The method of claim 1, wherein the information signal is generated by:

multiplying the first (V(t)) and the second (T(t)) output signals electronically to generate a combined signal; and feeding the combined signal and a reference signal (f(t)) into a lock-in amplifier (36).

4. The method of claim 1, wherein:

a first information signal is generated by feeding the first output signal (V(t)) and a reference signal (f(t)) into a lock-in amplifier (36b);

a second information signal is generated by feeding the second output signal (T(t)) and a reference signal(f(t) into a lock-in amplifier (36a); and the first and the second information signals are subsequently fed into a signal processing unit (20).

5. A system (10) for measuring heat changes in at least one sample and determining reaction parameters, comprising a measuring cell (16) for containing the sample during the measurement process, at least one electromagnetic radiation unit (14) for radiating one or several samples with modulated radiation (46) inside said measuring cell (16), wherein said measuring cell (16) includes at least one acoustic transducer (22) able to generate a first output signal (V(t)) and at least one heat measuring device (24) able to generate a second output signal (T(t)), which signals and a reference signal (f(t)) are able to be used as input signals to a combining unit (18) able to generate from said signals (V(t), T(t), f(t)) an information signal that is connectable to a signal processing unit (20) for determining the relevant reaction parameters.

6. The system of claim 5, wherein the combining unit (18) includes a first combining element (36) able to generate a combined signal of the first output signal (V(t)) and the reference signal (f(t)) and a second combining element (40) able to generate the information signal from the combined signal and said second output signal (T(t)).

7. The system of claim 5, wherein the combining unit (18) comprises a first combining element (36) able to generate a combined signal of the second output signal (T(t)) and the reference signal (f(t)), and a second combining element (40) able to generate the information signal from the combined signal and said first output signal (V(t)).

8. The system of claim 5, wherein the combining unit (18) comprises a module (52) able to generate a combined signal by adding the first output signal (V(t)) and the second output signal (T(t)) together, and a lock-in amplifier (36) able to generate the information signal from said combined signal and the reference signal (f(t)).

9. The system of claim 5, wherein the combining unit (18) comprises a module (54) able to generate a combined signal by multiplying the first output signal (V(t)) and the second output signal (T(t)) together, and a lock-in amplifier (36) able to generate the information signal from said combined signal and the reference signal (f(t)).

10. The system of claim 5, wherein the combining unit (18) comprises a first lock-in amplifier (36a) able to generate a first information signal of the first output signal (V(t)) and the reference signal (f(t)), and a second lock-in amplifier (36b) able to generate a second information signal from the second output signal (T(t)) and the reference signal (f(t)), wherein both information signals are connectable to a signal processing unit (20) as input signals for determining the relevant reaction parameters.

* * * * *